United States Patent
Suzuki et al.

(10) Patent No.: US 8,008,040 B2
(45) Date of Patent: Aug. 30, 2011

(54) PROCESS FOR PRODUCTION OF 5-ENE-3-ONE OR 3,6-DIONE DERIVATIVES OF STEROLS, PROCESSES FOR PRODUCTION OF LIPID METABOLISM IMPROVERS, FOODS, DRINKS, AND ANIMAL FEEDS, AND ANALYTICAL METHOD

(75) Inventors: Kunio Suzuki, Tokyo (JP); Tadashi Nagashima, Aichi (JP); Shinya Nagahashi, Aichi (JP)

(73) Assignee: Toyo Hakko Co., Ltd., Aichi (JP)

( * ) Notice: Subject to any disclaimer, the term of this patent is extended or adjusted under 35 U.S.C. 154(b) by 757 days.

(21) Appl. No.: 11/632,072

(22) PCT Filed: Jul. 12, 2005

(86) PCT No.: PCT/JP2005/012869
§ 371 (c)(1),
(2), (4) Date: Jun. 3, 2008

(87) PCT Pub. No.: WO2006/006608
PCT Pub. Date: Jan. 19, 2006

(65) Prior Publication Data
US 2008/0248520 A1      Oct. 9, 2008

(30) Foreign Application Priority Data
Jul. 14, 2004  (JP) ................................. 2004-207885

(51) Int. Cl.
*C12P 33/00*  (2006.01)
(52) U.S. Cl. .......................................................... 435/52
(58) Field of Classification Search .................. None
See application file for complete search history.

(56) References Cited

U.S. PATENT DOCUMENTS

2003/0153051 A1 * 8/2003 Aono et al. .................. 435/70.1

FOREIGN PATENT DOCUMENTS

| JP | H11-193296 | 7/1999 |
| JP | 2001-055333 | 2/2001 |
| JP | 2001-240544 | 9/2001 |
| WO | WO 99/45106 | 9/1999 |

OTHER PUBLICATIONS

Dai Kitamoto. "Reaction mechanism of cholesterol oxidase", Bioscience and Industry, vol. 57, No. 7, 1999, pp. 464-467.
Liu, et al. "Bioconversion of cholesterol to cholest-4-en-3-one in aqueous/organic solvent two-phase reactors", Enzyme and Microbial Technology, vol. 18, 1996, pp. 184-189.
Michihisa, et al. "Screening and application of organic solvent resistant-microorganisms", Bioscience and Industry, vol. 61, No. 1, 2003, pp. 17-21.
Yamashita, et al. "Separation of the two reactions, oxidation and isomerization, catalyzed by *Streptomyces* cholesterol oxidase", Protein Engineering, vol. 11, No. 11,1998, pp. 1075-1079.
Doukyu, et al. "Control with organic solvents of efficiency of persolvent cholesterol fermentation by *Pseudomonas* sp. strain ST-200", Biosci. Biotech. Biochem, vol. 60, No. 10, 1996, pp. 1612-1616.
Aono, R. et al., *Oxidative Bioconversion of Cholesterol by Pseudomonas sp. Strain ST-200 in a Water-Organic Solvent Two-Phase System*; Applied and Environmental Microbiology, vol. 60, No. 7, Jul. 1994, pp. 2518-2523.
Dong (1988) Separation of Mixed Sterol by High Performance Liquid Chromatography, Cereals & Oils, 3:40-41.
Razzazi-Fazeli et al. (2000) Determination of Cholesterol Oxides in Processed Food Using High-Performance Liquid Chromatography-Mass Spectrometry With Atmospheric Pressure Chemical Ionisation, J. Chromatogr. A., 896:321-334.

* cited by examiner

*Primary Examiner* — Herbert J. Lilling
(74) *Attorney, Agent, or Firm* — Morgan, Lewis & Bockius LLP

(57) ABSTRACT

An object of the present invention is to provide a process according to which 5-ene-3-one or 3,6-dione derivatives of sterols can be synthesized with a better yield, as well as a process for production of lipid metabolism improvers, foods, drinks, and animal feeds containing the 5-ene-3-one or 3,6-dione derivatives of sterols.

The process for production of 5-ene-3-one or 3,6-dione derivatives of sterols of the present invention involves preparing a culturing solution containing an *Arthrobacter* bacterium, which is a microorganism exhibiting a cholesterol oxidase activity, and then, adding to the culturing solution an equivalent amount of hexane so as to prepare a bilayer solution consisting of an aqueous layer and a hydrocarbon-based solvent layer. Thereafter, sterol, or a derivative thereof, is made as a substrate contained therein, a reaction performed with cholesterol oxidase at 30° C. for 2 days, and, ethanol then added to separate a hydrocarbon-based solvent layer. Thereafter, the layer is dried to a state of dryness by means of a vacuum dryer so as to obtain 5-ene-3-one or 3,6-dione derivatives.

5 Claims, No Drawings

US 8,008,040 B2

PROCESS FOR PRODUCTION OF 5-ENE-3-ONE OR 3,6-DIONE DERIVATIVES OF STEROLS, PROCESSES FOR PRODUCTION OF LIPID METABOLISM IMPROVERS, FOODS, DRINKS, AND ANIMAL FEEDS, AND ANALYTICAL METHOD

TECHNICAL FIELD

The present invention relates to a process for production of 5-ene-3-one or 3,6-dione derivatives of sterols, processes for production of lipid metabolism improvers, foods, drinks, and animal foods, and an analytical method. More particularly, the present invention relates to a process according to which, 5-ene-3-one or 3,6-dione derivatives of sterols superior in physiological actions such as correction of obesity and lipid metabolism can be synthesized with a better yield, as well as processes for production of lipid metabolism improvers, foods, drinks, and animal feeds containing the 5-ene-3one or 3,6-dione derivatives of sterols, as well as an analytical method according to which 5-ene-3-one and 3,6-dione derivatives of sterols can be simultaneously and effectively analyzed.

BACKGROUND ART

It is known that cholesterol derivatives have a variety of physiological actions and that they are currently used in a variety of fields such as medicines, foods, drinks and feeds. For example, the following Patent Document 1 discloses anti-obesity agents and lipid metabolism improvers containing 24-alkylchlestane-3-one or 24-alkylchlestene-3-one as an active ingredient. In addition, the following Patent Document 2 discloses anti-obesity agents and lipid metabolism improvers containing as an active ingredient 24-methylcholest-5-ene-3-one which is a 5-ene-3-one derivative of sterol. Further, it is known that, in comparison with a 4-ene-3-one derivative of sterol, a 5-ene-3-one derivative and a 3,6-dione derivative of sterol are superior in terms of obesity and lipid metabolism-correctional mechanisms.

As well a chemical synthesizing method, a biological method of synthesizing a cholesterol derivative by culturing a microorganism is also known. As a biological synthesizing method of synthesizing a cholesterol derivative, for example, the following Non-Patent Document 1 discloses that a cholest-4-ene-3-one is obtained with cholesterol oxidase which is an enzyme using cholesterol or a derivative thereof as a substrate. According to this method, a 5-ene-3-one derivative is obtained by means of an oxidizing reaction from cholesterol, or a derivative thereof, which serves as a substrate, and then, a 4-ene-3-one derivative is rapidly produced by means of an isomerization reaction. And, the following Non-Patent Document 2 describes a method of biologically converting cholesterol into cholest-4-ene-3-one by using a microorganism (*ARTHROBACTER*) of a nature that is capable of producing cholesterol oxidase in a bilayer system of an aqueous layer and an organic solvent.
[Patent Document 1] JP-A-11-193296
[Patent Document 2] JP-A-2001-240544
[Non-Patent Document 1] "Bioscience and Industry" Vol. 57 No. 7 ('99) 464-467
[Non-Patent Document 2] "Enzyme and Microbial Technology" 1996, Vol. 18:184-189

DISCLOSURE OF THE INVENTION

Problems to be Solved by the Invention

However, in a cholesterol oxidase, it is known that, in comparison with an isomerizing rate, an oxidizing rate is about several times to about several tens times smaller, and that a rate-determining step is in an oxidizing process. Therefore, in the case of the biological synthesizing method in the Non-Patent Document 1 in which cholesterol oxidase is used, a problem arises that isomerization rapidly progresses to a 4-ene-3-one derivative, and that a yield of a 5-ene-3-one derivative is extremely low. In addition, the Non-Patent Document 2 merely describes that a 4-ene-3-one derivative is obtained biologically, and there is no technical foundation to suggest that a yield of a 5-ene-3-one derivative is enhanced in the course of adopting a biological synthesizing method. Further, in the Non-Patent Documents 1 and 2, there is no disclosure regarding a biological synthesis of a 3,6-dione derivative. Accordingly, the development has been desired of a process for producing 5-ene-3-one and 3,6-dione derivatives of sterols, both of which are superior to earlier processed in terms of productivity.

The present invention has been made in view of the aforementioned circumstances, and objects thereof are to provide a process according to which 5-ene-3-one or 3,6-dione derivatives of sterols superior in terms of physiological action such as obesity and in lipid metabolism correctional mechanisms can be synthesized with a better yield, as well as processes for production of lipid metabolism improvers, foods, drinks and animal feeds containing the 5-ene-3-one or 3,6-dione derivatives of sterols, an analytical method according to which 5-ene-3-one and 3,6-dione derivatives of sterols can be simultaneously and effectively analyzed.

Means to Solve the Problems

In order to solve the aforementioned problems, the present inventors continued to study intensively, and, as a result, discovered, entirely unexpectedly, that in a bilayer solvent consisting of a hydrocarbon-based solvent layer of alkane or the like and an aqueous layer, by culturing a microorganism exhibiting cholesterol oxidase, or a cholesterol oxidase activity in which sterol and a derivative thereof is used as a substrate, 5-ene-3-one or 3,6-dione derivatives of sterols can be obtained with a higher yield than previously, and this has resulted in completion of the present invention. In addition, the present inventors discovered that, by specifying a mobile phase and a column temperature at a time of analysis of 5-ene-3-one and 3,6-dione derivatives of sterols, by means of a high performance liquid chromatography (hereinafter, referred to as "HPLC") it becomes possible to separate and measure 5-ene-3-one and 3,6-dione derivatives of sterols at the same time a process which has been previously difficult, and this has resulted in completion of the present invention.

The present invention is as follows:

[1] A process for producing 5-ene-3-one or 3,6-dione derivatives of sterols, by means of performing a reaction, by inclusion of sterol, or a derivative thereof, in a bilayer solution containing an aqueous layer including a cholesterol oxidase-containing solution, and a hydrocarbon solvent layer including a hydrocarbon solvent.

[2] The process for producing 5-ene-3-one or 3,6-dione derivatives of sterols according to [1] above, in which the cholesterol oxidase-containing solution is a culturing solution for a microorganism exhibiting a cholesterol oxidase activity.

[3] The process for producing 5-ene-3-one or 3,6-dione derivatives of sterols according to [2] above, in which the microorganism is one or two, or more, kinds of bacteria belonging to the *Arthrobacter* genus, the *Streptomyces* genus, the *Brevibacterium* genus, or the *Rhodococcus* genus, and the *Bacillus* genus.

[4] A process for producing lipid metabolism improvers, by means of inclusion of 5-ene-3-one or 3,6-dione derivatives of sterols obtained by the process according to [1] above.

[5] A process for producing foods and drinks, by means of inclusion of 5-ene-3-one or 3,6-dione derivatives of sterols obtained by the process according to [1] above.

[6] A process for producing animal feeds, by means of inclusion of 5-ene-3-one or 3,6-dione derivatives of sterols obtained by the process according to [1].

[7] A method of analyzing 5-ene-3-one and 3,6-dione derivatives of sterols, comprising separating and measuring 5-ene-3-one and 3,6-dione derivatives of sterols at the same time by means of a HPLC method according to which, a mixed solution is used as a mobile phase that has been obtained by mixing acetonitrile and isopropyl alcohol in a ratio of (3 to 5)/(5 to 7) based on a volume.

[8] The method of analyzing 5-ene-3-one and 3,6-dione derivatives of sterols according to [7] above, in which a temperature of a column in the course of using the HPLC method is 10 to 30° C.

EFFECTS OF THE INVENTION

By means of the process for producing 5-ene-3-one or 3,6-dione derivatives of sterols of the present invention, and by provision of the essential features described above, 5-ene-3-one or 3,6-dione derivatives of sterols superior in terms of physiological actions such as obesity and in lipid metabolism correction mechanism can be obtained with a higher yield than previously.

In addition, by means of the process for producing lipid metabolism improvers, foods, drinks, and animal feeds of the present invention, and by having the aforementioned essential features, lipid metabolism improvers, foods, drinks and animal feeds can be obtained that produce more effectively than previously the superior effects described above.

Further, according to the method of analyzing 5-ene-3-one and 3,6-dione derivatives of sterols of the present invention, simultaneous separation and measurement of 5-ene-3-one and 3,6-dione derivatives of sterols, which have in the past proved difficult, can be obtained by means of the HPLC method.

BEST MODE FOR CARRYING OUT THE INVENTION

The present invention will be explained below.

The "aqueous layer comprising a cholesterol oxidase-containing solution" constituting the "bilayer solution" in the present invention is a layer containing cholesterol oxidase in an aqueous solvent. The kind of aqueous solvent is not particularly limited as long as it is of a nature that it is not mixed with the hydrocarbon-based solvent, and that is separated into two layers. As the aqueous solvent, water is usually used.

The "cholesterol oxidase" is an enzyme which catalyzes a reaction between one molecule of 3β-hydroxysteroid and one molecule of an oxygen so as to produce a corresponding 3-oxosteroid and hydrogen peroxide (EC.1.1.3.6). As the cholesterol oxidase, natural cholesterol oxidase produced by a microorganism is usually used, but as long as it is of a nature that is capable of catalyzing the reaction described above, a cholesterol oxidase that has been altered by a genetic engineering procedure, such as an amino acid sequence, or a high-order structure, may be used.

The cholesterol oxidase-containing solution is usually prepared by directly adding cholesterol oxidase to an aqueous solvent. Alternatively, the solution may be prepared by adding to an aqueous solvent a microorganism exhibiting cholesterol oxidase activity, followed by culturing. In other words, the cholesterol oxidase-containing solution also includes a solution containing a microorganism exhibiting cholesterol oxidase activity.

The "microorganism" mentioned above need not be particularly limited to a certain kind, as long as it is a microorganism exhibiting cholesterol oxidase. Examples of such a "microorganism" include a basidiomycete of *Agaricus* and a *Coriolus versicolor*, a filamentous fungus of *Aspergillus* and *Monascus*, and bacteria belonging to the *Arthrobacter* genus, the *Streptomyces* genus, the *Brevibacterium* genus, the *Rhodococcus* genus, and the *Bacillus* genus. Specific examples of the microorganism include *Arthrobacter Simplex*, viz. *Nocardioidos Simplex*.

As the microorganism, a commercially available microorganism is usually used. Otherwise, as long as it exhibits a cholesterol oxidase activity, even a microorganism that has been mutated in a mycological manner, a process which can be secured by means of natural mutation or a artificial mutation, such as a chemical substance such as EMS (ethyl methanesulfonate), diethyl sulfate, NTG (N-methyl-N'-nitro-N-nitrosoguanidine) and nitrosoguanidine, or by an X-ray, a γ-ray or an ultraviolet-ray, can be utilized. Alternatively, a transformed microorganism can be used which has developed a capacity to express cholesterol oxidase, by transferring a gene encoding cholesterol oxidase into a microorganism such as *Escherichia coli* by means of a suitable vector so as to perform transformation.

As long as the activity of cholesterol oxidase has not deteriorated, a pH of the cholesterol oxidase-containing solution need not be particularly limited, and can be within various ranges, depending on the kind of cholesterol oxidase and the microorganism used. A pH of the cholesterol oxidase-containing solution is usually 5.0 to 9.0, preferably 6.0 to 8.0, and further preferably 6.5 to 7.5. Adjustment of a pH of the cholesterol oxidase-containing solution can be performed, for example, by addition of a basic solution such as an aqueous ammonium solution, an aqueous potassium hydroxide solution, an aqueous sodium hydroxide solution, an aqueous sodium carbonate solution, an aqueous potassium carbonate solution or the like, or an acidic solution such as phosphoric acid or the like.

The cholesterol oxidase-containing solution contains as an essential component the cholesterol oxidase or the microorganism exhibiting cholesterol oxidase activity, but may also contain other components as long as the effects of the action of the present invention are not adversely affected. For example, the solution may contain a carbon source, a nitrogen source, inorganic salts, an amino acid and a vitamin necessary for growth of the microorganism exhibiting cholesterol oxidase activity. Alternatively, the solution may contain a coenzyme for assisting the function of the cholesterol oxidase. Further, the solution may contain a pH-adjusting agent for adjusting a pH of the cholesterol oxidase-containing solution.

The contents of the cholesterol oxidase and the inoculation number of the microorganism in the cholesterol oxidase-containing solution need not be particularly limited, but as and when necessary, an appropriate content and an appropriate inoculation number can be selected.

As the "hydrocarbon-based solvent layer comprising a hydrocarbon-based solvent" constituting the "bilayer solution", a solvent can be used that is of a nature such that it need not be completely mixed with an aqueous layer constituting the bilayer solution, and can be separated into two layers. The "hydrocarbon solvent" may be any one of an aliphatic hydrocarbon, an alicyclic hydrocarbon, or an aromatic hydrocarbon-based solvent. Moreover, the hydrocarbon solvent may be of only one kind, or it may be a mixed solvent made up of two or more kinds. A carbon number of the "hydrocarbon solvent" also need not be particularly limited, but a hydrocarbon-based solvent can be used of normally a carbon number of 4 or more, of preferably a carbon number of 4 to 12, or further preferably a carbon number of 5 to 8. Examples of the hydrocarbon-based solvent include alkanes such as n-butane, n-hexane and heptane, and cycloalkanes such as cyclohexane. In addition, the hydrocarbon-based solvent may contain other substances as long as the effects of the action of the present invention are not inhibited.

In the present invention, a hydrocarbon-based solvent is added to an aqueous layer comprising a cholesterol oxidase-containing solution so as to prepare a bilayer solution consisting of two layers, an aqueous layer and a hydrocarbon-based solvent layer. When the bilayer solution is prepared, an order for adding the cholesterol oxidase-containing solution and the hydrocarbon-based solvent need not be particularly limited. For example, the cholesterol oxidase-containing solution may be added to the hydrocarbon-based solvent, or conversely, the hydrocarbon-based solvent may be added to the cholesterol oxidase-containing solution. In addition, a ratio of the aqueous layer and the hydrocarbon-based solvent layer in the bilayer solution need not be particularly limited, but, as and when appropriate, a variety of ranges may be adopted. A ratio (volumetric ratio) of the aqueous layer and the hydrocarbon-based solvent layer is usually 1:(0.2 to 2), preferably 1:(0.4 to 1.5), and further preferably 1:(0.5 to 1).

In the present invention, by inclusion of "sterol or a derivative thereof" as a substrate in the bilayer solution, a reaction is performed with the cholesterol oxidase. The kind of "sterol" need not be particularly limited, but, as and when appropriate, various derivatives can be used. Examples of the "sterol or a derivative thereof" include plant sterols (plant-derived sterols and derivatives thereof, e.g. β-sitosterol, campesterol, and stigmasterol), cholesterol, ergosterol, lanosterol, as well as cholestane-3-one, cholestene-3-one and derivatives such as 24-alkyl derivatives.

The method of inclusion of the "sterol or a derivative thereof" in the bilayer solution need not be particularly limited. For example, after the bilayer solution has been prepared, the "sterol or a derivative thereof" may be added. Alternatively, the "sterol or a derivative thereof" can be added to the cholesterol oxidase-containing solution, or to the hydrocarbon based solvent, before preparation of the bilayer solution, and the cholesterol oxidase-containing solution and the hydrocarbon-based solvent can be mixed. In this manner, the "sterol or a derivative thereof" may be introduced at the same time as the preparation of the bilayer solution.

The conditions for the reaction need not be particularly limited. For example, a reaction temperature is usually from 25° C. to 42° C., and preferably from 28° C. to 38° C. A reaction time is usually between 5 and 72 hours, and preferably between 24 and 48 hours. Further, during the course of the reaction, shaking or stirring may be appropriately performed.

The method of purifying and recovering 5-ene-3-one, or 3,6-dione, derivatives of sterols obtained by the present invention need not also be particularly limited, but as and when necessary derivatives can be recovered and purified by an appropriate means. Usually, within the reaction solution, a hydrocarbon solvent layer containing 5-ene-3-one, or 3,6-dione, derivatives of sterols is separated, and an active ingredient can as and when necessary be concentrated by a method such as solvent distillation, and then dried by an appropriate method such as lyophilization, spray drying or vacuum drying, thereby enabling derivatives to be recovered. Alternatively, in this purification and recovery method, the reaction solution, or the separated hydrocarbon solvent layer, can when necessary be treated by for example, passing it through a sterilization filter, thereby enabling sterilization treatment to be performed. In the recovery method, when an alcohol such as methanol, ethanol or the like is added to the reaction solution, it becomes easy to separate the reaction solution into two layers, an aqueous layer and a hydrocarbon solvent layer. As a result, purification and recovery of 5-ene-3-one or 3,6-dione derivatives of sterols become easy, and addition of the alcohol is thus preferable.

The "5-ene-3-one derivatives of sterols" obtained in the present invention need not be particularly limited in their structure as long as they have a double bond at a 5-position, and a ketone group at a 3-position, of a sterol skeleton. In addition, the "3,6-dione derivatives of sterols" obtained by the present invention need not be particularly limited in their structure as long as they have a ketone group at a 3-position and a 6-position of a sterol skeleton. For example, a sterol skeleton or a side chain may have an appropriate functional group such as an alkyl group (methyl group, ethyl group etc.). The number of double bonds need not be particularly limited, but a sterol skeleton or a side chain may have 1 or more, preferably 1 to 4, and further preferably 1 to 2 other double bonds.

Examples of the "5-ene-3-one derivatives of sterols" include 24-alkylcholest-5-ene-3-one, 24-alkylcholest-5,7-diene-3-one, 24-alkylcholest-5,8-diene-3-one, 24-alkylcholest-5,9(11)-diene-3-one, 24-alkylcholest-5,22-diene-3-one, 24-alkylcholest-5,7,22-triene-3-one, 24-alkylcholest-5,8,22-triene-3-one, 24-alkylcholest-5,9(11),22-triene-3-one, 24-alkylcholest-5,25(27)-diene-3-one and the like. Examples of the "alkyl" in the respective aforementioned substances include a methyl group and an ethyl group. Examples of the "3,6-dione derivatives of sterols" include 4-cholestene-3,6-dione, 4-campest-3,6-dione, and 24-alkylcholest-4-ene-3,6-dione.

The present invention may be performed for purposes of obtaining 5-ene-3-one derivatives, or for obtaining 3,6-dione derivatives. Further, in the present invention, since both of 5-ene-3-one and 3,6-dione derivatives can be obtained at the same time, the present invention may be performed for obtaining both of them at the same time.

A method of separating and measuring 5-ene-3-one and 3,6-dione derivatives of sterols obtained by the present invention need not be particularly limited, and as and when necessary various methods can be performed. Usually, the analytical method of the present invention, which will be described in detail below, can be used.

In comparison with 4-ene-3-one derivatives of sterols, 5-ene-3-one and 3,6-dione derivatives of sterols obtained by the present invention provide a superior degree of physiological action such as obesity- and lipid metabolism-correctional mechanisms. Therefore, 5-ene-3-one derivatives of sterols obtained by the present invention can be used for a variety of purposes. For example, they can be used as medicaments such as anti-obesity and lipid metabolism improvers, additives for foods and drinks, or additives for animal feeds. As a result, medicaments containing 5-ene-3-one sterols can be obtained such as anti-obesity agents and lipid metabolism improvers, health drinks or health foods producing obesity- and lipid metabolism-correctional mechanisms, livestock feeds or fish feeds for the purpose of improving the quality of meat, and pet foods for preventing obesity of pet animals.

The method of analyzing 5-ene-3-one and 3,6-dione derivatives of sterols of the present invention comprises separating and measuring 5-ene-3-one and 3,6-dione derivatives of sterols at the same time by a high performance liquid chromatography (HPLC) method using, as a mobile phase, a mixed solution obtained by mixing acetonitrile and isopropyl alcohol in a ratio of (3 to 5)/(5 to 7) based on volume.

In the method of analyzing 5-ene-3-one and 3,6-dione derivatives of sterols of the present invention, in the mixed solution, acetonitrile and isopropyl alcohol are used. Moreover, the ratio of acetonitrile and isopropyl alcohol is a ratio of (3 to 5)/(5 to 7), and preferably (3.5 to 4.5)/(5.5 to 6.5) based on volume. By adopting such a range, simultaneous separation and measurement of 5-ene-3-one and 3,6-dione derivatives of sterols, which has previously proved difficult, can be achieved. In addition, according to the HPLC method, other conditions need not be particularly limited, but, as and when appropriate, a kind, a length and a temperature of a column, and a flow rate of a mobile phase can be within a variety of ranges. For example, from a viewpoint of efficiency of separation and action, a length of a column can be from 20 cm to 80 cm, and preferably from 40 cm to 60 cm. In addition, a temperature of a column can be 10° C. to 30° C., preferably from 15° C. to 25° C. Further, a flow rate of a mobile phase is preferably from 0.1 ml/min to 5 ml/min, and more preferably from 0.1 ml/min to 1 ml/min.

EXAMPLES

The present invention will now be specifically explained by Examples.

As a pre-culturing medium, an aqueous liquid medium (pH; 7.0±0.1) having a composition described in the following Table 1 (A) was prepared. As a regular culturing medium, an aqueous liquid medium (pH; 7.0±0.1) having the composition described in the following Table 1 (B) was prepared. Further, as bacterial cells, the commercially available *Arthrobacter Simplex*, which is a gram-positive *bacillus*, was used.

TABLE 1

| Table 1 | |
|---|---|
| Component | Content (%) |
| (A) Pre-culturing medium | |
| Glucose | 1 |
| Yeast extract | 0.5 |
| $K_2HPO_4$ | 0.2 |
| $MgSO_4 \cdot 7H_2O$ | 0.05 |
| $NH_4Cl$ | 0.3 |
| $FeSO_4 \cdot 7H_2O$ | 0.001 |
| Purified water | Balance |
| (B) Regular culturing medium | |
| Sorbitol | 0.5 |
| Yeast extract | 1 |
| $K_2HPO_4$ | 0.1 |
| $MgSO_4 \cdot 7H_2O$ | 0.05 |
| $NH_4Cl$ | 0.2 |
| KCl | 0.1 |
| $FeSO_4 \cdot 7H_2O$ | 0.001 |
| PHS-FK | 0.1 |
| O-10V | 0.1 |
| Hexane | 0.0013 |

One platinum loop of the bacterial cells was scraped from an active slant, and inoculated on a pre-culturing medium. Subsequently, the bacterial cells were shaken and cultured for 2 days under conditions of 30° C. and about 180 rpm. Then, the pre-culturing medium was inoculated on the regular culturing medium so that an inoculation concentration became about 2%. Culturing was then continued for 2 days at a level of ventilation of 1 VVM, a pH of 7.0±0.2, a temperature of 30° C.±0.3, rotation of a wing of 250 rpm, under conditions of appropriate adjustment of dissolution in oxygen. Thereupon, as a cholesterol oxidase inducing agent, 0.1% of "PHS-FK" (manufactured by Tama Biochemical Co., Ltd.) which is one kind of plant sterol, and 0.1% of an emulsifier "O-10V" (manufactured by Kao Corporation) were added.

After completion of culturing, in order to prepare a bilayer solution consisting of an aqueous layer and a hydrocarbon-based solvent layer, to 100 ml of the regular culturing medium was added an equivalent amount of hexane and, further, a substrate described in the following Table 2 was added so as to produce a final concentration of 1%. Then, after closure of the regular culturing medium, the reaction was continued for a period of 2 days while stirring to an extent such that an upper layer and a lower layer were mixed. After completion of the reaction, ethanol in an amount which was twice the amount of the bilayer solution, was added, the mixture was stirred, ethanol was further added little by little, and the upper layer (hydrocarbon-based solvent layer) and the lower layer (aqueous layer) were separated. After the lower layer was completely removed, the upper layer was passed through a sterilization filter and then dried to a state of dryness by means of a vacuum dryer so as to recover a product as a powder. The product was then analyzed by HPLC. The results are shown in Table 2. As a Comparative Example, according to the same manner as that described above, except insofar that cholesterol was used as a substrate, and hexane was not added, a reaction was performed, and a product was analyzed. Results are also shown in the following Table 2.

HPLC analysis of a product was performed by the following method.

Acetonitrile and isopropyl alcohol were mixed at a ratio of 4/6 (volume standard), and by use of an aspirator to prepare a mobile phase degassed at a reduced pressure. Then, the mobile phase was passed at an amount which was ten times the amount of a column volume, so as to equilibrate a column. A baseline was monitored, and stabilized, and equilibration of a column was thus completed.

The product was then weighed precisely, and was dissolved in the mobile phase to 0.2% (v/v). After dissolution, the solution was treated with a filter (0.42 μm) so as to obtain a HPLC sample. HPLC was performed under the following conditions.

[HPLC Conditions]
Column; "Cadenza CD C-18" (4.6×500 mm; manufactured by Imtakt Corporation)
Flow rate; 0.55 ml/min
Detector and detection wavelength; "UV detector" 210 nm
Column temperature; 18° C.
Sample dissolving solvent; same as mobile phase
Injection amount; 20 μl The contents of each component in a sample were calculated from a value of the resulting peak area and a calibration curve, and the concentration of each component was measured by means of the following equation.

The concentration of each component (%, v/v)="the content of each component in the sample calculated from the calibration curve"×100/40

TABLE 2

Table 2

|  | Kind of substrate | Content (%) of product in products | | |
|---|---|---|---|---|
|  |  | 4-Ene derivatives | 5-Ene derivatives | 3,6-Dione derivatives |
| Example 1 | Cholesterol | 21 | 4 | Trace |
| Example 2 | Plant sterol (PHS-FK) | 18 | 4.9 | 1.1 |
| Comparative Example 1 | Cholesterol* | 14 | ND | ND |

*A surfactant was added so as to suspend a substrate, and this was followed by a reaction (without the addition of an organic solvent at the time of reaction)

From Table 2, as illustrated in Comparative Example 1, when a reaction was performed without a hexane layer serving as a hydrocarbon-based solvent, it can be observed that only 4-ene derivatives, were obtained, and that 5-ene derivatives and 3,6-dione derivatives which are an object of the present invention, could not be obtained.

On the other hand, in Example 1 in which a reaction was performed by adding cholesterol as a substrate to a bilayer solution consisting of an aqueous layer comprising a cholesterol oxidase-containing solution and a hexane layer serving as a hydrocarbon-based solvent, in contrast to Comparative Example 1, 5-ene derivatives could be obtained. In addition, when plant sterol is used as a substrate, as shown in Example 2, it can be observed that not only 5-ene derivatives, but also 3,6-dione derivatives, could be obtained.

The present invention is not limited to the aforementioned specific Examples and, within the scope of the present invention, varying kinds of embodiments are possible, depending on the purpose and the application, Examples can be variously changed.

INDUSTRIAL APPLICABILITY

By means of the present invention 5-ene-3-one derivatives and 3,6-dione derivatives of sterols with superior physiological actions such as obesity- and lipid metabolism-correctional mechanisms, can be effectively produced. The present invention can be appropriately applied in such fields as foods and drinks, medicines and animal feeds.

The invention claimed is:

1. A process for production of 5-ene-3-one of sterols, comprising steps of:
    performing a reaction, by inclusion of sterol or a derivative thereof in a bilayer solution containing of an aqueous layer including a cholesterol oxidase-containing solution and a hydrocarbon-based solvent layer including a hydrocarbon-based solvent,
    wherein the cholesterol oxidase-containing solution is a culturing solution for a *Arthrobacter* genus exhibiting a cholesterol oxidase activity.

2. The process for production of 5-ene-3-one of sterols according to claim 1, wherein the hydrocarbon-based solvent is at least one selected from n-butane, n-hexane, heptane and cycloalkanes.

3. The process for production of 5-ene-3-one of sterols according to claim 1, further comprising adding an alcohol to a reaction solution after the reaction is terminated.

4. The process for production of 5-ene-3-one of sterols according to claim 1, wherein the sterol is plant sterols.

5. The process for production of 5-ene-3one of sterols according to claim 1, wherein the *Arthrobacter* genus is *Arthrobacter Simplex*.

\* \* \* \* \*